(12) United States Patent
Li et al.

(10) Patent No.: US 8,298,584 B2
(45) Date of Patent: Oct. 30, 2012

(54) BIOPOLYMERIC MEMBRANE FOR WOUND PROTECTION AND REPAIR

(75) Inventors: Shu-Tung Li, Oakland, NJ (US); Natsuyo Shishido Lee, Bridgewater, NJ (US); Debbie Yuen, Woodcliff Lake, NJ (US)

(73) Assignee: Collagen Matrix, Inc., Franklin Lakes, NJ (US)

( * ) Notice: Subject to any disclaimer, the term of this patent is extended or adjusted under 35 U.S.C. 154(b) by 622 days.

(21) Appl. No.: 12/346,482

(22) Filed: Dec. 30, 2008

(65) Prior Publication Data

US 2010/0166823 A1 Jul. 1, 2010

(51) Int. Cl.
*A61K 8/65* (2006.01)
*A61K 38/00* (2006.01)

(52) U.S. Cl. ......... 424/489; 424/472; 424/492; 530/356
(58) Field of Classification Search .................. None
See application file for complete search history.

(56) References Cited

U.S. PATENT DOCUMENTS

| 5,026,381 A | 6/1991 | Li |
| 5,206,028 A | 4/1993 | Li |
| 5,374,539 A | 12/1994 | Nimni et al. |
| 5,741,257 A | 4/1998 | Kirsch |
| 5,951,535 A | 9/1999 | Fujiwara et al. |
| 5,997,895 A | 12/1999 | Narotam et al. |
| 6,090,996 A | 7/2000 | Li |
| 6,179,872 B1 | 1/2001 | Bell et al. |
| 6,391,333 B1 | 5/2002 | Li et al. |
| 6,679,913 B2 | 1/2004 | Homsy |
| 6,712,851 B1 | 3/2004 | Lemperle et al. |
| 6,974,862 B2 | 12/2005 | Ringeisen et al. |
| 6,977,231 B1 | 12/2005 | Matsuda |
| 7,049,348 B2 | 5/2006 | Evans et al. |
| 7,060,103 B2 | 6/2006 | Carr, Jr. et al. |
| 7,112,417 B2 | 9/2006 | Vyakarnam et al. |
| 7,374,777 B2 | 5/2008 | Li et al. |
| 2006/0088578 A1* | 4/2006 | Li et al. ................ 424/443 |
| 2007/0155009 A1* | 7/2007 | McClelland et al. ......... 435/325 |
| 2009/0030070 A1* | 1/2009 | Kida et al. .................. 514/456 |
| 2009/0166580 A1* | 7/2009 | Tanaka et al. ............. 252/182.12 |
| 2009/0269586 A1* | 10/2009 | Parma et al. ............... 428/411.1 |

FOREIGN PATENT DOCUMENTS

| EP | 1016757 | 7/2000 |
| WO | WO 93/11803 | 6/1993 |
| WO | WO 2006046414 A1 * | 5/2006 |

OTHER PUBLICATIONS

Merriam-Webster Dictionary (2012, updated) "On", ://www.merriam-webster.com/dictionary/on, pp. 1-2.*

* cited by examiner

*Primary Examiner* — Anand Desai
*Assistant Examiner* — Samuel Liu
(74) *Attorney, Agent, or Firm* — Occhiuti Rohlicek & Tsao LLP

(57) ABSTRACT

The present invention relates to a conformable and semipermeable biopolymeric membrane suitable for tissue repair and protection. This membrane contains a first layer made from randomly oriented, reconstituted biopolymer fibers and, on top of the first layer, a coating layer made from biopolymer fibers.

14 Claims, No Drawings

BIOPOLYMERIC MEMBRANE FOR WOUND PROTECTION AND REPAIR

BACKGROUND OF THE INVENTION

Surgical procedures cause wounds at the target sites. For example, neural surgery often results in wounds at the dura mater, i.e., the membrane covering the brain and spinal cord. Biopolymeric membranes facilitate wound healing and protect wounds from invasion of fibrotic cells.

SUMMARY OF THE INVENTION

The present invention features a biopolymeric membrane suitable for repairing wounds. The biopolymeric membrane includes at least two layers: (1) a first layer including randomly oriented fibers of a first biopolymer (e.g., collagen, elastin, fibrin, chitosan, alginic acid, cellulose, or glycosaminoglycan), the fibers having a length of 2.5-50 cm (e.g., 10-40 cm); and (2) a second layer including fibers of a second biopolymer (e.g., collagen, elastin, fibrin, chitosan, alginic acid, cellulose, or glycosaminoglycan), the fibers having a length of 0.05-3 mm (e.g., 0.1-1.0 mm). The membrane has a draping angel of 30-90 degree (e.g., 45-90 degree or 60-90 degree), a hydrothermal shrinkage temperature of 48-72° C. (e.g., 50-70° C.), and is permeable to molecules having a molecular weight less than 100,000 daltons (e.g., <70,000 daltons or <29,000 daltons). It can further contain one or more bioactive agents, e.g., various growth factors and antibiotics.

In one example, the biopolymeric membrane of this invention has a thickness ranging from 0.1 mm to 3.0 mm (e.g., 0.3-1.5 mm, or 0.3-0.7 mm), and a density of 0.04-0.6 g/cm$^3$ (e.g., 0.1-0.4 g/cm$^3$ or 0.2-0.4 g/cm$^3$).

This invention also features a method of making the biopolymeric membrane described above. The method includes the following steps: (i) dispersing fibers of a first biopolymer in an acidic or alkaline solution to form a mixture; (ii) neutralizing, if necessary, the mixture to a pH equal to the isoelectric point of the first biopolymer to produce reconstituted fibers of the first biopolymer; (iii) dehydrating the reconstituted fibers of the first biopolymer; (iv) compressing the dehydrated fibers to form a first layer; (v) freeze-drying the first layer; (vi) coating the freeze-dried first layer with fibers of a second biopolymer to produce a membrane, the fibers of the second biopolymer forming a second layer on the first layer; and (vii) crosslinking the fibers of the first biopolymer and the fibers of the second biopolymer in the membrane. When collagen is used as the first biopolymer, the collagen fibers are dispersed in a solution having a pH value either lower than 3 or higher than 11 to form a mixture. The mixture is then neutralized to a pH of 4.5-6 (e.g., 5.0-5.5) to produce reconstituted collagen fibers.

The details of one or more embodiments of the invention are set forth in the description below. Other features or advantages of the present invention will be apparent from the following detailed description of several embodiments, and also from the appended claims.

DETAILED DESCRIPTION OF THE INVENTION

The present invention relates to a bioresorbable, conformable, and semi-permeable biopolymeric membrane for tissue protection and repair, e.g., for repairing wounds at the dura mater in patients who have undergone neural surgery.

In one embodiment, the biopolymeric membrane of this invention has two layers. The first layer contains randomly oriented fibers made from a first biopolymer. The fibers used for making this layer are reconstituted so that they are longer than their un-reconstituted counterparts. The second layer, i.e., the coating layer, is formed by coating the first layer with fibers made from a second biopolymer. This layer is very thin, i.e., having a thickness of only 1-50 μm (e.g., 3-20 μm).

Both the first layer and the second layer can be fabricated by fibers made from various biopolymers, which can be naturally occurring or artificial. Examples of the biopolymers include any types of collagen, elastin, fibrin, chitosan, alginic acid, cellulose, and glycosaminoglycan. Type I collagen is preferred given its biocompatibility and availability. The first layer and the second layer can contain fibers of the same biopolymer or fibers of different biopolymers.

The two-layer biopolymer membrane described above can further contain one or more bioactive agents, e.g., growth factors and antibiotics. The bioactive agent(s) can form an additional layer either in between the first and second layers described above, or on the surface of the membrane. Alternatively, the bioactive agent(s) is interspersed in the first or second layer.

The biopolymeric membrane of this invention possesses the following features.

First, it is highly conformable, i.e., having a draping angle ranging from 30 to 90 degree. The draping angle of a membrane is determined as follows. Fix one half of a membrane onto a horizontal surface and allow the other half to drape via gravity. The angle between the draped half and the horizontal surface is assigned as the draping angle of the membrane. Possessing a high conformability, the biopolymeric membrane of this invention can be used to substantially seal a wound site that has an irregular shape and a non-smooth contour.

Second, the biopolymeric membrane of this invention is semi-permeable, i.e., permeable only to molecules having a molecule weight less than 100,000 dalton. As such, this membrane protects a wound site from cell invasion but allows passage of small nutrient molecules through it.

Third, the membrane is stable in vivo; namely, it has a hydrothermal shrinkage temperature in the range of about 48 to about 72° C. (corresponding to an in vivo resorption time of 2-12 months).

It is preferred that the membrane possesses a suture pullout strength of 0.1-0.7 kg (e.g., 0.15-0.5 kg), a tensile strength of 5-100 kg/cm2 (e.g., 20-50 kg/cm$^2$), and a density of 0.04-0.60 g/cm$^3$ (e.g., 0.04-0.3 g/cm$^3$).

Given the above-described features, the biopolymeric membrane of this invention is suitable for facilitating wound healing and occluding cell invasion. Particularly, this biopolymeric membrane is useful as an onlay graft for dura repair.

The biopolymer membrane of this invention can be prepared as follows:

Fibers made from the first biopolymer are dispersed in an acidic (e.g., pH<3) or alkaline (e.g., pH>11) solution to form a mixture. The biopolymer fibers can be either isolated from their natural sources or synthesized chemically. Suitable acidic solutions include solutions prepared with an organic acid, e.g., acetic acid and lactic acid, or with an inorganic acid, e.g., hydrochloric acid and sulfuric acid. When an alkaline solution is used, it can be prepared using sodium hydroxide, potassium hydroxide, or calcium hydroxide.

Next, the mixture is neutralized to a pH value equal to the isoelectric point of the first biopolymer, i.e., within 20% of the isoelectric point of that biopolymer. At this pH, the biopolymer fibers mentioned above reconstitute to form fibers having a length greater than 5 cm. The reconstituted fibers, separated from the liquid phase of the mixture, are then partially dehydrated to remove the liquid using a meshed screen or a similar device via a mechanical force. The extent of this partial dehydration determines the conformability and density of the membrane to be made. The reconstituted fibers are then compressed to form a sheet with desired thickness, size, and wet weight. These factors also determine the density of the resultant membrane. The sheet can then freeze dried to form the first layer with a Virtis freeze dryer via methods known in the art. See, e.g., U.S. Pat. No. 5,026,381.

Subsequently, the first layer is coated by spraying on it a dispersion containing fibers made from a second biopolymer, which can be prepared by the method described above. The biopolymer fibers contained in this dispersion has a low content and a short fiber length so that they can form mist particles during spraying without blocking the nozzle of the spray apparatus. The spraying step can be performed using any spray apparatus that can deposit mist-like polymer particles onto the surface of the first layer without affecting its biomechanical characteristics. Suitable spray apparatuses include commercially available sprayers, air brushes, or custom-designed sprayers. Upon spraying, the fibers of the second biopolymer form a coating layer (i.e., the second layer) on the first layer to produce a two-layer membrane. The thickness of the coating layer, generally ranging from about 1 μm to about 50 μm, controls permeability. When necessary, the coating step can be repeated so as to achieve the desired thickness and permeability.

Finally, the two-layer membrane described above is cross-linked to affix the biopolymer fibers, thus producing a biopolymeric membrane of this invention. The fibers can be cross-linked by a chemical cross-linking agent (e.g., an aldehyde compound or a carbodimiide). Formaldehyde is a preferred cross-linking agent, given its high vapor pressure and its safe use in implantable devices. Alternatively, the fibers can also be cross-linked by heat and vacuum, ultraviolet, or low-dose gamma irradiation.

When a cross-linking agent is used, the extent of the cross-linking can be controlled by the concentration of the cross-linking agent, the time for the cross-linking reaction, and the temperature (if the agent is in liquid form), or the vapor pressure (if the agent is in gas form), under which the cross-linking reaction is taken. The extent of the cross-linking controls the in vivo resorption time of the membrane.

If desired, one or more bioactive agents can be incorporated into the biopolymeric membrane described herein. The bioactive agent(s) can be mixed with fibers of the second biopolymer and interspersed into the second layer, or is sprayed (for agents in liquid form) or dusted (for agents in powder form) on the second layer. Alternatively, it is mixed with the fibers of the first biopolymer and interspersed into the first layer, or is sprayed/dusted on the first layer prior to the formation of the second layer described above. The first layer is then covered with the second layer on the surface where the bioactive agent(s) stays to form a sandwich-structured membrane having the bioactive agent(s) in between the first and second layer. The thickness of the second layer controls the release rate of the bioactive agent(s). The release rate is also controlled by factors such as the agent's particle size, hydrophilicity, and interaction with the biopolymer fibers included in either the first or the second layer.

Below is an example of making the biopolymeric membrane of this invention, using collagen. Collagen fibers are prepared from collagen rich tissues, e.g., skin, bone, tendon, and ligament, via methods known in the art. See, e.g., U.S. Pat. No. 5,512,291; and Oneson, et al., J. Am. Leather Chemists Assoc. 65:440-450, 1970. They are then dispersed in an acidic solution to form a collagen dispersion. See U.S. Pat. Nos. 3,157,542 and 5,326,350. Alternatively, the collagen dispersion can be prepared by mixing collagen fibers in an alkaline solution. The preferable collagen content in the collagen dispersion ranges from 0.5% to 1.5% by weight. Normally, the length of the collagen fibers in the dispersion thus prepared is less than 3 mm.

The collagen dispersion is then neutralized to a pH value of 4.5-6 (e.g., 5). At this pH, the collagen fibers reconstitute to form long collagen fibers having a fiber length of 10-40 cm. The reconstituted collagen fibers are then partially dehydrated and subsequently compressed to form a collagen sheet. After being freeze dried, the collagen sheet is coated via spray with a collagen dispersion containing unreconstituted collagen fibers to produce a collagen membrane. In this dispersion, the collagen content is preferably less than 0.1% and the collagen fibers have a length less than 1 mm. The collagen membrane is then treated with formaldehyde to cross link the collagen fibers contained in the membrane.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Preparation and Characterization of a Conformable and Semi-Permeable Collagen Membrane Preparation of Purified Collagen Fibers The fat and fascia of bovine flexor tendon were carefully removed and washed with water. The cleaned tendon was frozen and comminuted by slicing into 0.5 mm slices with a meat slicer. One kilogram of sliced wet tendon was first extracted in 5 liters of distilled water at room temperature for 24 hours. The extractant was discarded and 5 liters of 0.2 M HCl in 0.5 M $Na_2SO_4$ was added and the tendon slices were extracted at room temperature for 24 hours. The acid solution was discarded and 5 liters of 0.5 M $Na_2SO_4$ was added to wash the tendon and to remove the residual acid. The acid extracted tendon was then extracted in 5 liters of 0.75 M NaOH in the presence of 1 M $Na_2SO_4$ at room temperature for 24 hours. The base solution was then discarded. The residual base was neutralized with 3 M HCl to pH 5 followed by several changes of distilled water to remove the residual salts associated with the tendon. The tendon was then defatted with isopropanol (tendon:isopropanol=1:5, v/v) for 24, 46, and 6 hours at 25° C. under constant agitation. The extractant was decanted and an equal volume of isopropanol was added and the tendon slices were extracted overnight at 25° C. under constant agitation. The defatted tendon was then dried under a clean hood. The purified collagen fibers were stored dry at room temperature until further processing.

Preparation of Collagen Fiber Dispersions

Purified collagen fibers were weighed and dispersed in 0.07 M lactic acid, homogenized with a Silverson Homogenizer (East Longmeadow, Mass.), and then filtered with a stainless steel mesh filter (30 mesh). The dispersion, which had a collagen content of 0.7% (w/v), was de-aerated with vacuum to remove the trapped air.

Alternatively, purified collagen fibers were weighed and dispersed in 0.005 M NaOH, homogenized with a Silverson Homogenizer (East Longmeadow, Mass.), and then filtered with a stainless steel mesh filter (40 mesh). The dispersion, which had a collagen content of 1.0% (w/v), was deaerated with vacuum to remove the air trapped in it.

Reconstitution of Collagen Fibers

Acid dispersed collagen fibers (180 g) were mixed with 20 ml 0.6% $NH_4OH$ to form a solution having a pH value of 4.7-5.0 (i.e., the isoelectric point of collagen) to produce reconstitute collagen fibers. The reconstituted collagen fibers have a fiber length of 2.5-50 cm.

Fabrication of a Conformable and Semi-Permeable Collagen Membrane

The reconstituted collagen fibers described above were partially dehydrated using a stainless steel screen by gently squeezing the water out from the wet fibers to a weight that gives a density in the range of 0.2 to 0.25 g of collagen/$cm^3$. The partially dehydrated fibers were then compressed into a sheet membrane using a roller. The membrane was freeze-dried (10° C. for 24 hours, 20° C. for 16 hours at a pressure less than 200 millitorr) using a Virtis Freeze Dryer (Gardiner, N.Y.). The dried membrane of collagen fibers was hung vertically in a chamber and sprayed with 0.05% (w/v) lactic acid dispersed collagen fibers. Care was taken to ensure that the surface was uniformly coated with a thin layer of collagen fibers. The collagen-fiber coated membrane was dried in air and then crosslinked with formaldehyde vapor, generated from 0.1% formaldehyde solution at ambient temperature, for 6 hours.

Characterization of the Conformable and Semipermeable Collagen Membrane

Physical, chemical, and mechanical characteristics of the membranes described in the proceeding example were assessed in the following ways:

i) Thickness

The thickness of the membranes was determined with a caliper.

ii) Density

The density (g/$cm^3$) of a membrane was determined as follows. The membrane was first dried under vacuum for 24 hours or over $P_2O_5$ for 24 hours and the dry weight recorded. The length, width, and thickness of the membrane were then measured with a caliper. The density is calculated using the formula: (weight of the membrane)/(volume of the membrane).

iii) Hydrothermal Shrinkage Temperature ($T_s$)

A circular sample of the membrane was punched, hydrated in a phosphate buffer with a concentration of 0.01M, and a pH of 7.4, sealed in an aluminum cell, placed in a differential scanning calorimeter (DSC, Metter-Toledo, Inc., Columbus Ohio), and heated at a rate of 5° C./min. The temperature, at which the collagen in the membrane started losing its triple helical structure, was recorded as the hydrothermal shrinkage temperature.

iv) Suture Pullout Strength

The suture pullout strength of the membrane was determined with a tensile tester (Chatillon, Greensboro, N.C.) as follows. The membrane was cut to a size of 20 mm×15 mm and soaked in a phosphate buffered saline solution (pH 7.4) at 25° C. for about 2 minutes. A suture (3-0 silk black braided, taper SH-1, Ethicon, Somerville, N.J.) was placed through the membrane at a position approximately 4 mm from the 20 mm edge. One end of the suture was tied into a knot and the other end of the suture was secured to a hook adapter of the tensile tester. After the sample was fixed onto a clamp, the suture was pulled at a speed of 2.5 cm/min until it was pulled out. The strength to pull out the suture (i.e., the suture pullout strength) was recorded by the tensile tester.

v) Tensile Strength

Tensile strength of the membrane was also determined by the tensile tester described above. The membrane was cut into a dumbbell shape with a die punch and soaked in a phosphate buffered saline solution (pH 7.4) at 25° C. for about 2 minutes. The sample was then secured onto a clamp fixture, and pulled at a speed 2.5 cm/min until the sample was pulled apart. The strength under which the membrane was pulled apart was recorded as the tensile strength.

vi) Permeability

A 2-cm diameter disk cut from the membrane was inserted into a hole between two compartments (i.e., compartment 1 and compartment 2) of a chamber, thereby completely separating the two compartments. A fixed volume of PBS containing 50 μg carbonic anhydrase (having a molecule weight of 29,000 dalton) per ml was added to compartment 1 and a fixed volume of PBS was added to compartment 2. After equilibrated for 24 hours, the PBS in compartment 2 was determined for the percent of carbonic anhydrase contained therein by the carbonic anhydrase assay system described in Li, S. T., et. al., Biotechnology and Polymers: 281-293, 1991.

vii) Surface Characteristics

Surface morphology (i.e., macroscopic and microscopic structures of the membrane surface) was determined with a scanning electron microscope (SEM) at various magnifications.

Certain characteristics (average±standard deviation) of the biopolymeric membrane described herein are summarized below:

| Density (g/$cm^3$) [6] | Thickness of the layer made from reconstituted collagen fibers (mm) [20] | Thickness of the coating layer (μm) [6] | Percent of permeated carbonic anhydrase in 24 hrs [6] | Hydrothermal shrinkage temp. (° C.) [13] | Suture pull-out strength (kg) [6] | Tensile strength (kg/$cm^2$) [6] | Surface Morphology |
|---|---|---|---|---|---|---|---|
| 0.30 ± 0.06 | 0.43 ± 0.08 | 3.7 ± 0.4 | 7.8 ± 2.1 | 52 ± 1.0 | 0.21 ± 0.01 | 28.5 ± 6.8 | Smooth |

* The number in [ ] represents the number of samples tested

EXAMPLE 2

Use of a Conformable and Semipermeable Collagen Membrane in Neural Surgery for Dura Repair and Regeneration The collagen membrane prepared by the method described in Example 1 is used to promote dura repair and regeneration in a rabbit model. New Zealand white rabbits (3 to 4 kg) are anesthetized using xylazine (5 mg/kg) and ketamine (35 mg/kg) via intramuscular injection and maintained sedated using halothane (0.5 to 2%) via endotracheal tube. Their scalps are shaved and washed with Betadine. Under aseptic conditions, the scalps are incised coronally to expose the perioseum. The periosteum is then stripped from the calvarium using a periosteal elevator. Two medial and 2 lateral 2.1 mm burr holes are placed to avoid the sagittal and transverse venous sinuses and orbital cavity. Bone wax and electrocautery are used to control bleeding. A Dremel motor tool is used to cut a trapezoid-shaped craniotomy and elevate the bone flap hinged on the pericranium and the muscles attached to it. The bone flaps are removed with care to avoid damage to the underlying meninges and cerebral cortex. Using a dural hook, the dura mater is gently lifted and incised. Angled irridectomy scissors are used to create an 8 mm×8 mm damaged area in the dura mater. The collagen membrane, cut into a size of 1 cm², is soaked in sterile saline for 5 minutes and placed over the damaged area (1 mm overlap on dura) without suturing. The bone flaps are replaced and the periosteum is closed with a 3-0 chromic gut while the scalps are closed with a 2-0 vicryl suture.

OTHER EMBODIMENTS

All of the features disclosed in this specification may be combined in any 2 5 combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A biocompatible membrane for tissue repair, comprising:
    a first layer including randomly oriented fibers of a first biopolymer, the fibers of the first biopolymer having a fiber length ranging from 2.5 cm to 50 cm, and
    a second layer on top of a surface of the first layer, the second layer including fibers of a second biopolymer, the fibers of the second biopolymer having a fiber length ranging from 0.1-1.0 mm,
    wherein said biocompatible membrane has a thickness of 0.1 mm to 3.0 mm, a density of 0.04 to 0.60 g/cm³, a hydrothermal shrinkage temperature of 48-72° C., a draping angle of 30 to 90 degrees, and is permeable to molecules with a molecular weight of less than 100,000 daltons.

2. The biocompatible membrane of claim 1 wherein the first biopolymer is collagen, elastin, fibrin, chitosan, alginic acid, cellulose, or glycosaminoglycan.

3. The biocompatible membrane of claim 2, wherein the first biopolymer is collagen.

4. The biocompatible membrane of claim 3, wherein the second biopolymer is collagen.

5. The biocompatible membrane of claim 4, wherein the fibers of the first biopolymer have a length of 10-40 cm, and wherein the biocompatible membrane has a thickness of 0.3 mm to 1.5 mm, a density of 0.1 to 0.4 g/cm³, a hydrothermal shrinkage temperature of 50-70° C., a draping angle of 45 to 90 degrees, and is permeable to molecules with a molecular weight less than 70,000 daltons.

6. The biocompatible membrane of claim 5, wherein the membrane has a thickness of 0.3 mm to 0.7 mm, a density of 0.20 to 0.40 g/cm³, and is permeable to molecules with a molecular weight less than 29,000 daltons.

7. The biocompatible membrane of claim 1, wherein the fibers of the first biopolymer have a length ranging from 10 cm to 40 cm.

8. The biocompatible membrane of claim 1, wherein the second biopolymer is collagen, elastin, fibrin, chitosan, alginic acid, cellulose, or glycosaminoglycan.

9. The biocompatible membrane of claim 8, wherein the second biopolymer is collagen.

10. The biocompatible membrane of claim 1, wherein the membrane has a thickness ranging from 0.3 mm to 1.5 mm.

11. The biocompatible membrane of claim 1, wherein said membrane is permeable to molecules with a molecular weight of less than 70,000 daltons.

12. The biocompatible membrane of claim 1, further comprising a bioactive agent.

13. The biocompatible membrane of claim 1, wherein the second layer has a thickness of 1 μm to 50 μm.

14. The biocompatible membrane of claim 13, wherein the second layer has a thickness of 3 μm to 20 μm.

* * * * *